United States Patent [19]

Dovichi et al.

[11] Patent Number: 5,415,841
[45] Date of Patent: May 16, 1995

[54] CONTINUOUS BIOCHEMICAL REACTOR FOR ANALYSIS OF SUB-PICOMOLE QUANTITIES OF COMPLEX ORGANIC MOLECULES

[75] Inventors: Norman J. Dovichi; Karen C. Waldron, both of Edmonton, Canada

[73] Assignee: Governers of the University of Alberta, Edmonton, Canada

[21] Appl. No.: 292,605

[22] Filed: Aug. 18, 1994

Related U.S. Application Data

[63] Continuation of Ser. No. 69,125, May 28, 1993, abandoned.

[51] Int. Cl.$^6$ ............................................. G01N 33/68
[52] U.S. Cl. ............................. 422/68.1; 422/69; 422/70; 422/81; 422/101; 422/103; 422/107; 422/116; 436/89; 436/94; 436/177; 436/178
[58] Field of Search ................. 422/64, 68.1, 69, 102, 422/107, 116, 58, 59, 66, 88, 81, 101, 103, 211, 241, 190, 70; 436/89, 94, 164, 174, 177, 178

[56] References Cited

U.S. PATENT DOCUMENTS

| | | | |
|---|---|---|---|
| 4,603,114 | 7/1986 | Hood et al. | 436/89 |
| 4,610,847 | 9/1986 | Hood et al. | 422/102 |
| 4,704,256 | 11/1987 | Hood et al. | 422/68 |
| 4,935,624 | 6/1990 | Henion et al. | 250/288 |

OTHER PUBLICATIONS

Nolan et al., Subfemtomole Detection Limit for Amino Acid Determination with Laser-Induced Crossed-Beam Thermal Lens Detection; *Analytical Chemistry*, vol. 59, No. 23, Dec. 1, 1987; pp. 2803–2805.

Green et al., Design Of A Variable Wavelength UV Absorption Detector For On-Column Detection In Capillary Electrophoresis And Comparison Of Its Performance To A Fixed Wavelength UV Absorption Detector; *Journal of Liquid Chromatography*, vol. 12, No. 13; pp. 2527–2561, 1989.

Needleman, Ed, Protein Sequence Determination, A Sourcebook of Methods and Techniques; Second Revised Edition and Enlarged Edition, Chapter 8, pp. 232–385; 1985.

Smith, Automated Synthesis and Sequence Analysis of Biological Macromolecules; *Analytical Chemistry*, vol. 60, No. 6; pp. 381A–390A; Mar. 15, 1988.

(List continued on next page.)

*Primary Examiner*—Jeffrey R. Snay
*Assistant Examiner*—Harold Y. Pyon
*Attorney, Agent, or Firm*—Christensen O'Connor Johnson & Kindness

[57] ABSTRACT

A novel reactor for reacting and subsequently analyzing sub-picomole quantities of a sample organic molecule. The reactor includes a continuous capillary connected between two valves that control fluid flow in the capillary. One part of the capillary forms a reaction chamber where the sample may be immobilized for subsequent reaction with reagents supplied through the valves. Another part of the capillary passes through or terminates in the detector portion of an analyzer such as an electrophoresis apparatus, liquid chromatographic apparatus or mass spectrometer. The apparatus may form a peptide or protein sequencer for carrying out the Edman degradation reaction and analyzing the reaction product produced by the reaction. The protein or peptide sequencer includes a reaction chamber for carrying out coupling and cleavage on a peptide or protein to produced derivatized amino acid residue, a conversion chamber for carrying out conversion and producing a converted amino acid residue and an analyzer for identifying the converted amino acid residue. The reaction chamber may be contained within one arm of a capillary and the conversion chamber is located in another arm of the capillary. An electrophoresis length of capillary is directly capillary coupled to the conversion chamber to allow electrophoresis separation of the converted amino acid residue as it leaves the conversion chamber. Identification of the converted amino acid residue takes place at one end of the electrophoresis length of the capillary.

19 Claims, 11 Drawing Sheets

OTHER PUBLICATIONS

Capillary electrophoresis, Instrumentation '91; *C&EN;* pp. 28, 35, Mar. 18, 1991.

Kent et al., Overview: Approaches to Sub-Picomole Protein Sequencing; *BioTechniques,* vol. 5, No. 4; pp. 314–321, 1987.

Hewick et al., A Gas–Liquid–Solid Phase Peptide and Protein Sequenator; *The Journal of Biological Chemistry,* vol. 256, No. 15; pp. 7990–7997, Aug. 10, 1981.

Bhown, Ed., Protein/Peptide Sequence Analysis: Current Methodologies; Chapter 5, Gas Phase Sequence Analysis Of Proteins/Peptides; CRC Press, Inc.; pp. 87–117; 1988.

Bornhop et al., Simultaneous Laser-Based Refractive Index and Absorbance Determinations within Micrometer Diameter Capillary Tubes; *Analytical Chemistry,* vol. 59, No. 13; pp. 1632–1636; Jul. 1, 1987.

Long et al., Thermal Lens Technique: A New Method of Absorption, Spectroscopy; *Science,* vol. 191; pp. 183–185, Jan. 16, 1976.

Liang et al., Covalent Immobilization Of Proteins and Peptides for Solid-Phase Sequencing Using Prepacked Capillary Columns; *Analytical Biochemistry,* vol. 188; pp. 366–373; 1990.

Cheng et al, Subattomole Amino Acid Analysis by Capillary Zone Electrophoresis and Laser-Induced Fluorescence, *Science,* vol. 242, pp. 562–564, 1988.

Swerdlow et al., Three DNA Sequencing Methods Using Capillary Gel Electrophoresis and Laser-Induced Fluorescence, *Analytical Chemistry,* vol. 63, No. 24, 2835–2841; Dec. 15, 1991.

Yu et al., Attomole Amino Acid Determination by Capillary Zone Electrophoresis with Thermooptical Absorbance Detection; *Analytical Chemistry,* vol. 61, No. 1; pp. 37–40, Jan. 1, 1989.

Waldron et al., Sub-Femtomole Determination of Phenylthiohydantoin–Amino Acids: Capillary Electrophoresis and Thermooptical Detection, Reprinted from *Analytical Chemistry,* vol. 64, No. 13, pp. 1396–1399, Jul. 1, 1992.

Drossman et al., High-Speed Separations of DNA Sequencing Reactions by Capillary Electrophoresis; *Analytical Chemistry;* vol. 62, pp. 900–903, 1990.

Maeda et al., Reaction of Fluorescein–Isothiocyanate with Proteins and Amino Acids, part I; *The Journal of Biochemistry,* vol. 65, No. 5, pp. 777–783, 1969.

Kawauchi et al, Reaction of Fluorescein-Isothiocyanate with Proteins and Amino Acids, part II; *The Journal of Biochemistry,* vol. 66, No. 6, pp. 783–789, 1969.

Muramoto et al., The Application of Fluorescein Isothiocyanate and High-Performance Liquid Chromatography for the Microsequencing of Proteins and Peptides, *Analytical Biochemistry,* vol. 141, pp. 446–450, 1984.

Knoll, Estimation of the Limit of Detection in Chromatography; *Journal of Chromatographic Science,* vol. 23, 4 pages, Sep. 1985.

Tempst et al., Examination of Automated Polypeptide Sequencing Using Standard Phenyl Isothiocyanate Reagent and Subpicomole High-Performance Liquid Chromatographic Analysis; *Analytical Biochemistry,* vol. 183, pp. 290–300, 1989.

Cohen et al., High-Performance Capillary Electrophoretic Separation of Bases, Nucleosides, and Oligonucleotides: Retention Manipulation via Micellar Solutions and Metal Additives; *Analytical Chemistry,* vol. 59, No. 7, pp. 1021–1027, Apr. 1, 1987.

Liu et al., Capillary electrophoretic separations of peptides using micelle–forming compounds and cyclodextrins as additives; *Journal of Chromatography,* vol. 519, pp. 189–197, 1990.

Terabe et al., Electrokinetic Separations with Micellar Solutions and Open-Tubular Capillaries; *Analytical Chemistry,* vol. 56, No. 1, pp. 111–113, 1984.

Mikkers et al., Concentration Distributions In Free Zone Electrophoresis; *Journal Of Chromatography,* vol. 169, pp. 1–10, 1979.

Loo et al., Primary Sequence Information from Intact Proteins by Electrospray Ionization Tandem Mass Spectrometry; *Science,* vol. 248, pp. 201–204, Apr. 13, 1990.

Jeno et al., CRC: Laboratory Methodology in Biochemistry Amino Acid Analysis and Protein Sequencing; Chapter 5, Application Of 4-N, N-Dimethylaminoazobenzene-4'-Isothiocyanate (Dabitc) To The Structure Determination Of Peptides And Proteins; pp. 63–81.

Aebersold et al., Covalent Immobilization of Proteins for High-Sensitivity Sequence Analysis: Electroblotting onto Chemically Activated Glass from Sodium Dodecyl Sulfate–Polyacrylamide Gels; *Biochemistry,* vol. 27, pp. 6860–6867, 1988.

OTHER PUBLICATIONS

McGuffin et al., Aids For Analytical Chemists: Nanoliter Injection System for Microcolumn Liquid Chromatography; *Analytical Chemistry*, vol. 55, No. 3; pp. 580–583, Mar. 1983.

Kettler et al., Pulsed–Laser Photothermal Refraction Detection in Capillary Liquid Chromatography; *Analytical Chemistry*, vol. 59, No. 13; pp. 1733–1736, Jul. 1, 1987.

Otsuka et al., Electrokinetic Chromatography With Micellar Solutions Separation of Phenylthiohydantoin–Amino Acids; *Chromsymp.* 617, pp. 219–226, ©1985 Elsevier Science Publishers, B.V.

Swerdlow et al., Capillary gel electrophoresis for DNA sequencing, Laser–induced fluorescence detection with the sheath flow cuvette; *Journal of Chromatography*, vol. 516, pp. 62–67, 1990.

Jorgensen et al., Capillary Zone Electrophoresis; *Science*, vol. 222, pp. 266–272; Oct. 21, 1983.

Wu et al., High–Sensitivity Fluorescence Detector For Fluorescein Isothiocyanate Derivatives Of Amino Acids Separated By Capillary Zone Electrophoresis; *Journal of Chromatography*, vol. 480, pp. 141–155, 1989.

Rohlicek et al., Simple Apparatus For Capillary Zone Electrophoresis And Its Application To Protein Analysis; *Journal of Chromatography*, vol. 494, pp. 87–98, 1989.

Sweedler et al., Fluorescence Detection in Capillary Zone Electrophoresis Using a Charge–Coupled Device with Time–Delayed Integration; *Analytical Chemistry*, vol. 63, No. 5; pp. 496–502, Mar. 1, 1991.

Monnig et al., On–Column Sample Gating for High–Speed Capillary Zone Electrophoresis; *Analytical Chemistry*, vol. 63, No. 8; pp. 802–807, Apr. 15, 1991.

Waldron et al., Capillary zone electrophoresis separation and laser–based detection of both fluorescein thiohydantoin and dimethylaminoazobenzene thiohydantoin derivatives of amino acids; *Electrophoresis*, vol. 11, pp. 777–780, 1990.

Bruno et al., Thermo–Optical Absorption Detection in 25-μm–i.d. Capillaries: Capillary Electrophoresis of Dansyl–Amino Acids Mixtures; *Applied Spectroscopy*, vol. 45, No. 3; pp. 462–467, 1991.

Wu et al., Capillary Zone Electrophoresis Separation And Laser–Induced Fluorescence Detection Of Zeptomole Quantities Of Fluorescein Thiohydantoin Derivatives Of Amino Acids; *Talanta*, vol. 39, No. 2, pp. 173–178, 1992.

Wu et al., Capillary Zone Electrophoresis Separation And Laser–Induced Fluorescence Detection Of Zeptomole Quantities of Fluorescein Thiohydantoin Derivatives Of Amino Acids; *Talanta*, vol. 39, No. 2; pp. 173–178, 1992.

Aebersold et al., Covalent Attachment of Peptides for High Sensitivity Solid–Phase Sequence Analysis; *Analytical Biochemistry*, vol. 187, pp. 56–65, 1990.

CONTINUOUS BIOCHEMICAL REACTOR FOR ANALYSIS OF SUB-PICOMOLE QUANTITIES OF COMPLEX ORGANIC MOLECULES

This application is a continuation application based on copending application Ser. No. 08/069,125, filed on May 28, 1993.

FIELD OF THE INVENTION

This invention relates to biochemical reactors and methods of operating biochemical reactors.

BACKGROUND AND SUMMARY OF THE INVENTION

Analysis of minute (sub-picomole) quantities of various organic molecules, as for example proteins, oligosaccharides, peptides, nucleotides, amino acids and DNA is of great value in many environmental, biotechnological, medical and pharmaceutical applications. In many cases, the available sample is very small, rendering analysis difficult and time consuming. Particularly this is the case where a small quantity of protein or peptide has been isolated and it is desired to identify the protein or peptide by determining the sequence of amino acids in the protein or peptide.

The basic chemistry of sequencing a peptide or a protein is known as Edman degradation chemistry, after P. Edman, *Arch. Biochem. Biophys.* 22, 475 (1979). In the Edman degradation reaction, the first step is a coupling step in which a peptide or protein (hereinafter described simply as a peptide) is first treated with a peptide degradation coupling agent such as phenylisothiocyanate (PITC), which couples to the peptide or protein to form a coupled peptide. The next step is a cleavage step in which the coupled peptide is treated with anhydrous acid, such as anhydrous trifluoroacetic acid (TFA), to cleave the coupled peptide to produce an amino acid residue, such as cyclic thiazolinone amino acid (ATZ), and leaving a truncated peptide, the peptide having had one amino acid residue cleaved from the peptide. In the next step, a conversion step, the amino acid residue is separated from the truncated peptide and treated with an aqueous solution or conversion agent, typically an aqueous acid such as aqueous TFA, to produce a converted amino acid residue, such as phenyl thiohydantoin (PTH) amino acid. The converted amino acid residue carries an amino acid that has been cleaved from the peptide. In the final step, identification, the cleaved amino acid is identified by some appropriate means.

An example of an apparatus for carrying out the Edman degradation reaction and sequencing a protein or peptide is described in R. Hewick et al, *A Gas-Liquid-Solid Peptide and Protein Sequencer*, The Journal of Biological Chemistry, Vol. 256, no. 15, Aug. 10, 1981, pp. 7990–7997. In the Hewick device as described in this paper, the sample peptide or protein is immobilized in a reaction chamber having a diameter of about 6 mm formed from a pair of facing conical cavities at the end of two facing glass rods. Capillaries, having diameter of about 0.5 mm, in the centers of the respective glass rods, supply reagent to and remove products from the reaction chamber. Coupling and cleavage are carried out in the reaction chamber and the derivatized amino acid residue is removed from the reaction chamber to a conversion flask, where the conversion step is carried out. The converted amino acid residue is then taken from the conversion flask, and the converted amino acid is identified by liquid chromatography. Further summary of the manner of operation of such an apparatus is described by M. W. Hunkapiller, in *Protein/Peptide Sequence Analysis: Current Methodologies*, A. S. Brown, ed., CRC Press Inc., Boca Raton La., 1988, at 87.

The entire degradation cycle of the Hewick apparatus requires in the order of 45 minutes, and has limited sensitivity. Further, the Hewick device requires relatively large quantities of reagent, which reduces its effectiveness for analyzing very small (femtomole, or $10^{-15}$ mole, or less) quantities of converted amino acid residue, in effect rendering it incapable of sequencing less than 1 picomole ($10^{-12}$ mole) of peptide.

The inventors have proposed a novel reactor for reacting and subsequently analyzing sub-picomole quantities of a sample organic molecule. The reactor includes a continuous capillary connected between two valves that control fluid flow in the capillary. One part of the capillary forms a reaction chamber where the sample may be immobilized for subsequent reaction with reagents supplied through the valves. Another part of the capillary passes through or terminates in the detector portion of an analyzer such as an electrophoresis apparatus, liquid chromatographic apparatus or mass spectrometer.

The apparatus may form a peptide or protein sequencer for carrying out the Edman degradation reaction and analyzing the reaction product produced by the reaction. The protein or peptide sequencer includes a reaction chamber for carrying out coupling and cleavage on a peptide or protein to produce derivatized amino acid residue, a conversion chamber for carrying out conversion and producing a converted amino acid residue and means for identifying the converted amino acid residue. In one aspect of the invention, unlike in the Hewick device, the reaction chamber is contained within one arm of a capillary and the conversion chamber is located in another arm of the capillary. In a further aspect of the invention, an electrophoresis length of capillary is directly capillary coupled to the conversion chamber to allow electrophoresis separation of the converted amino acid residue as it leaves the conversion chamber. Identification of the converted amino acid residue takes place at one end of the electrophoresis length of the capillary.

In one aspect of a method according to the invention, the Edman degradation reaction is carried out in a capillary. Immobilization, cleavage and coupling of the peptide/protein takes place in a reaction chamber portion of the capillary to produce derivatized amino acid residue, and conversion takes place in a conversion chamber portion of the capillary to produce a converted amino acid residue. Electrophoresis separation of the converted amino acid residue then preferentially takes place in an electrophoretic length of the same capillary, including by applying an electric field across the conversion chamber, followed by identification of the converted amino acid residue.

BRIEF DESCRIPTION OF THE DRAWINGS

There will now be described preferred embodiments of the invention, with reference to the drawings, by way of illustration, in which like numerals denote like elements and in which.

DETAILED DESCRIPTION OF PREFERRED EMBODIMENTS

As used in this patent document, a capillary is a small tube or pipe defined by one or more members of arbitrary cross-sectional shape suitable for fluid flow, such as circular. A capillary for use in analyzing sub-picomole quantities of sample should be no more than 1 mm inside diameter (circular bore) and preferably less than 530 μm inside diameter. A sample is the material that is to be analyzed or sequenced, and in the case of sequencing a peptide or protein is the peptide or protein to be sequenced. After reaction of the sample with a reagent, the product of the reaction will be referred to as a reaction product, which in the case of peptide or protein sequencing is the amino acid residue.

Figure 1:
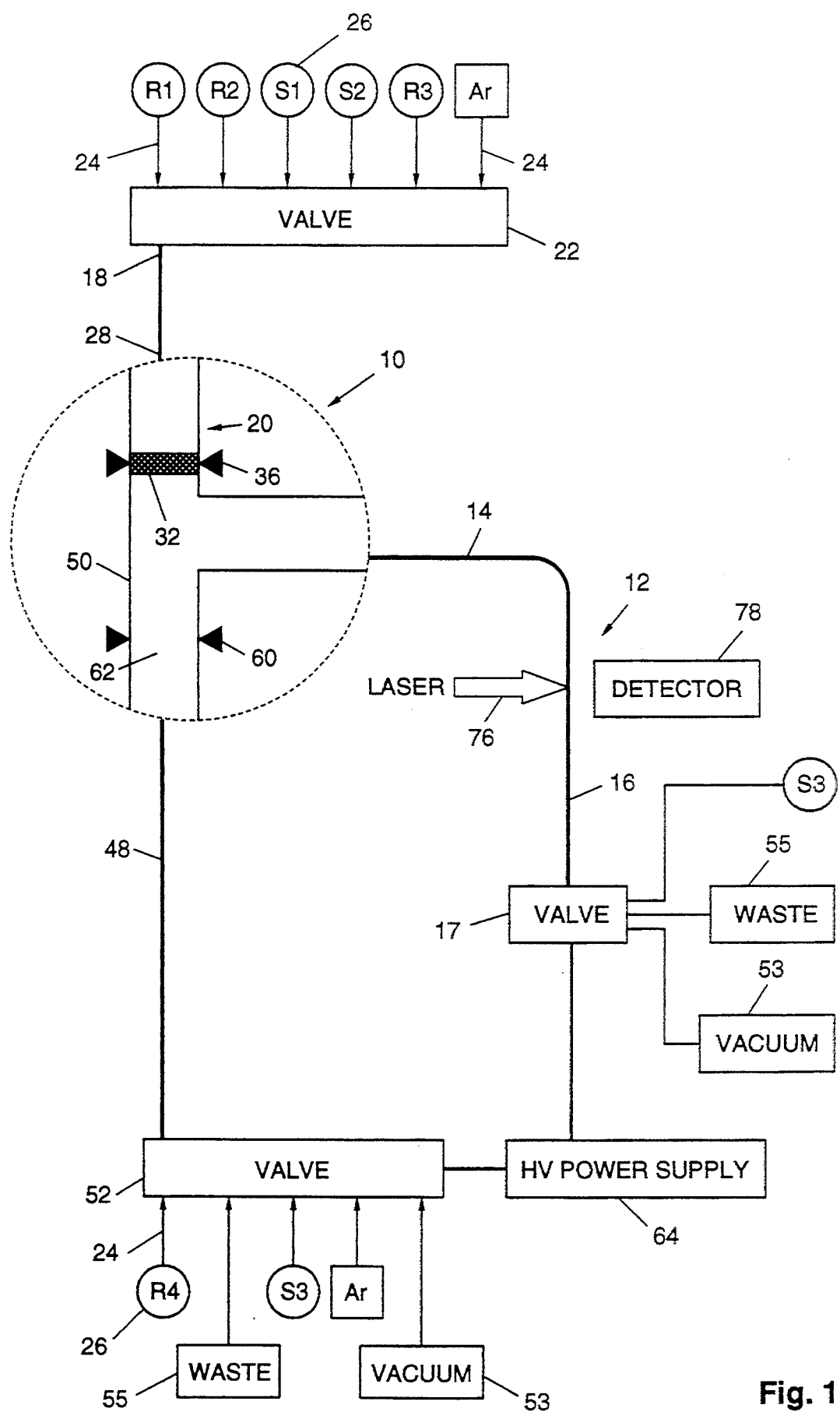
FIG. 1 is a schematic of one embodiment of a biochemical reactor and analyzer according to the invention, showing the reactor enlarged.

Referring to FIG. 1 there is shown a schematic of a combined reactor and analyzer specifically designed for peptide and protein sequencing. The reactor is shown enlarged at 10 and the analyzer is shown at 12. The reactor 10 and analyzer 12 are connected by an arm of a primary capillary 14 that provides a continuous flow path between the reactor 10 and analyzer 12. The analyzer 12 is located at one end 16 of the primary capillary 14 and is used for identification of a sample. A pneumatically actuated multi-position distribution valve 22, such as are used for capillary liquid chromatography and as may be obtained for example from Valco Instruments Co. Inc. of Houston, Tex., is connected at its common inlet/outlet port to a reaction end 18 of the primary capillary 14 and is used for delivery of reagents into the primary capillary 14. Other ports of the valve 22 are connected via suitable lines 24 such as Teflon tubes to vials 26 (containing fluids identified by the identifiers R1, R2, R3, R4, S1, S2 and S3, where S refers to solvent and R refers to reagent), to a source of argon gas Ar, to waste through line 55 or to a vacuum pump 53, according to the requirements of the reaction to be carried out in the reactor. As known in the art, a suitable inert gas is used to pressurize the vials 26 and deliver the reagent into the capillary 14. The delivery of small volumes of reagent may be managed using the split injection technique of Novotny (V. L. McGuffin and M. V. Novotny, Anal. Chem., 55, 580 (1983)). The valve 22, lines 24 and vials 26 together with the waste line 55, vacuum pump 53 and argon source form a means for controlling fluid flow in the capillary 14. Except as otherwise stated in this document, each valve located at the end of a capillary is a multi-position distribution valve of the same type as used for valve 22, as for example valve 17 connected to the identification end 16 of the capillary 14. The arm of the capillary 14 connecting the reaction arm 28 to the identification end 16 is preferably a fused silica tube having 50 μm inside diameter (ID) and 190 μm outside diameter (OD).

Figure 5:
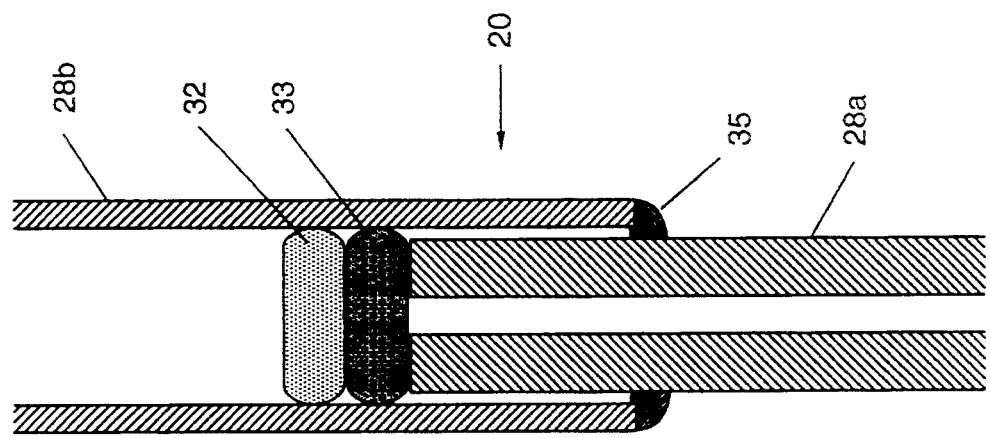
FIG. 5 is a section through another reaction chamber for use with the biochemical reactors shown in FIGS. 1, 2, 3, 6, 9 and 10.
Figure 4:
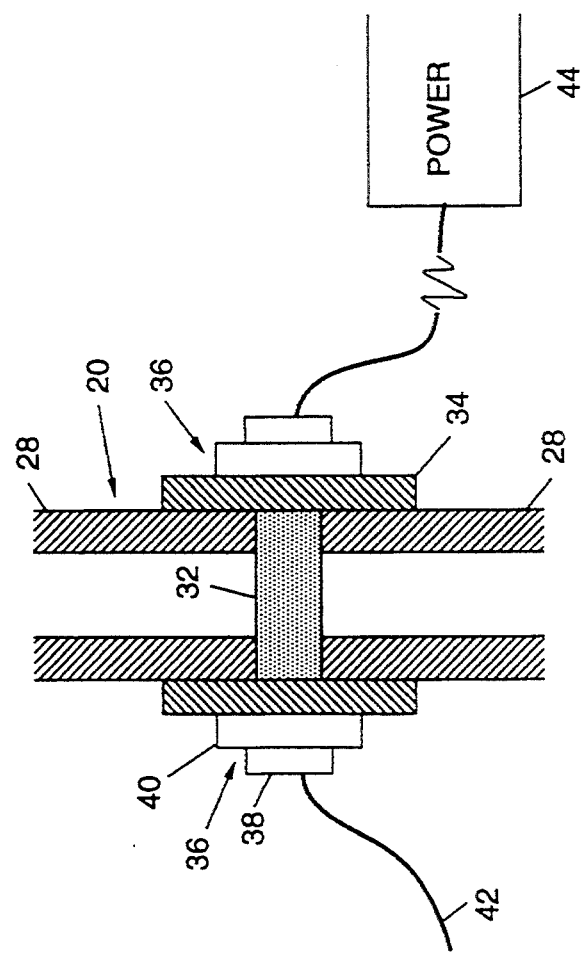
FIG. 4 is a section through a reaction chamber for use with the biochemical reactors shown in FIGS. 1, 2, 3, 6, 9 and 10.

A glass fibre reaction mat 32, or other suitable means for holding a sample such as a peptide or protein in the capillary 14, is fixed within arm 28 of the primary capillary 14 adjacent the reaction end 18. The location of the glass fibre reaction mat 32 defines a reaction chamber 20 within the capillary. A polymeric quaternary ammonium salt, such as Polybrene TM (hexadimethrine bromide), is impregnated into the reaction mat 32. The Polybrene attaches to the reaction mat and to peptides or proteins (or other samples) to immobilize the peptides or proteins in the reaction chamber 20 while allowing reagents to flow through the reaction mat 32. The reaction mat 32 may be held in place in the capillary 14 as shown in FIGS. 4 or 5 for example. Other chemical methods of attachment of a peptide may also be used, as for example for solid phase sequencing, methods as described in Aebersold, R., *Covalent Attachment of Peptides for High Sensitivity Solid Phase Sequence Analysis*, Analytical Biochemistry, 187, pp. 55–65, 1990, may be used.

In FIG. 4, the reaction mat 32 is sandwiched between two pieces of fused silica capillary 28 (for example, 100 μm ID, 245 μm OD) over which is pushed a short piece of fused silica capillary 34 having for example 250 μm ID. The pushing of the sandwiched mat into the capillary having larger inside diameter may be used to effectively cut the mat. A heater 36 formed for example of a thermocouple 38 (Peltier device), with brass heat sink 40, connected by leads 42 to a suitable power source 44, is located about the capillary arm 28 at the reaction chamber 20.

In FIG. 5, the capillary 28 is formed from a 50 μm ID, 360 μm OD capillary 28a on one side of the reaction chamber 20 and a 400 μm ID, 525 μm OD, fused silica capillary 28b on the other side, held together with epoxy 35. Glass fibre filter disc 32 pre-cycled with polybrene, is placed on top of a circular porous PTFE membrane 33, both resting and held by force of gravity on the top of the capillary 28a and by compression against the sides of the capillary.

Figure 6:
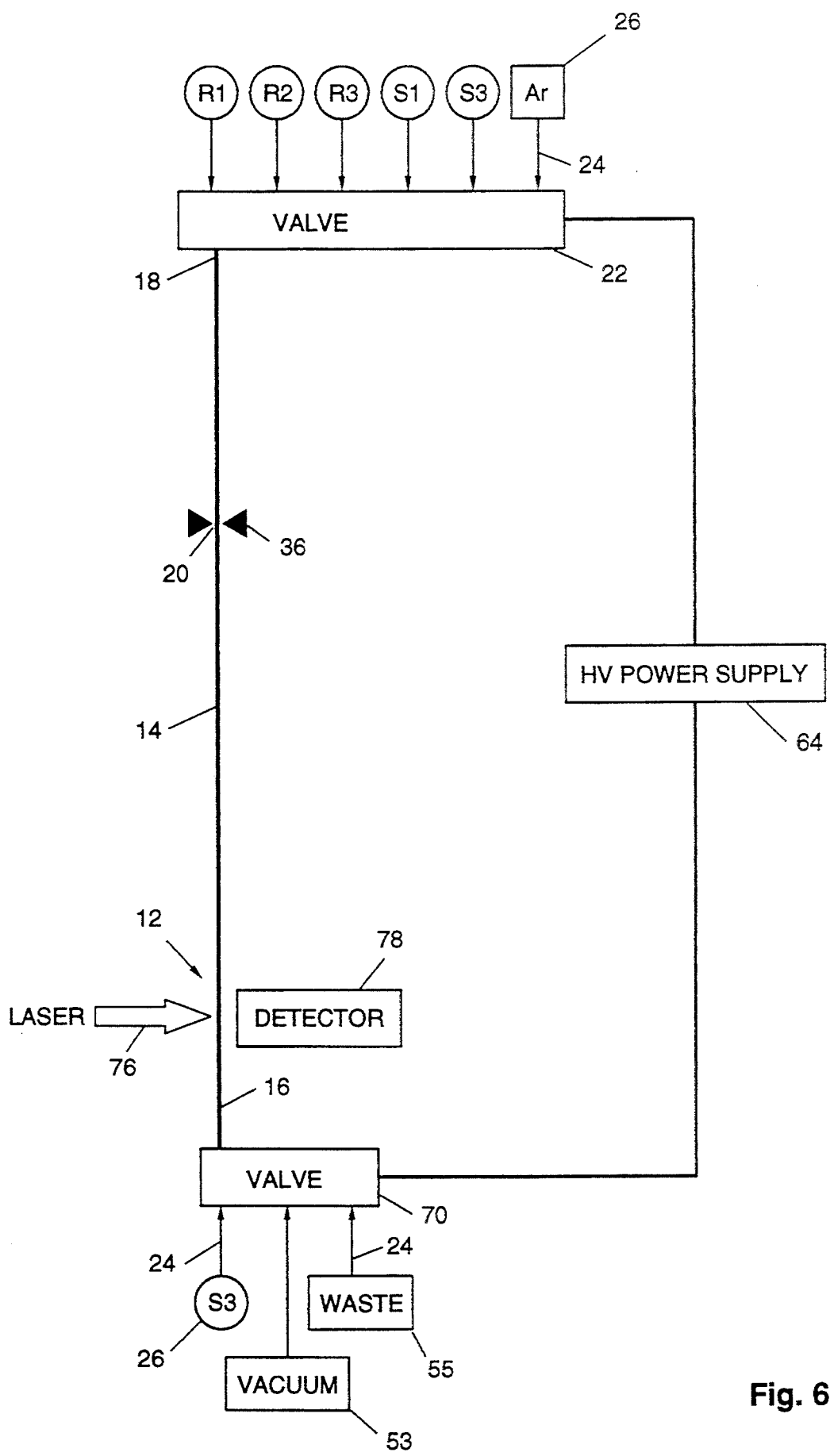
FIG. 6 is a schematic of another embodiment of a biochemical reactor and analyzer according to the invention having no conversion chamber (second reaction chamber)

In cases where derivatives of a reacted sample are directed immediately to the identification end of the capillary for analysis (as for example where identification of only the N-terminal end of a peptide is required), the capillary 14 may require no other inlet for reagents other than valve 22 (see FIG. 6). However, in the case where for example a protein or peptide is to be sequenced using the Edman degradation reaction, and the manner of analysis of the amino acid requires use of a fluid (electrophoresis medium for example) that will react with the peptide or protein, then it is necessary to isolate the peptide or protein in the reaction chamber during analysis, while the fluid may be flushed through the rest of the capillary 14.

In such a situation, a supply arm 48 of the capillary 14 having one end meeting the reaction arm 28 at junction 50 may be used for delivery of reagent. Isolation of the reaction arm 28 of the capillary 14 may be obtained by a suitable valve on the arm 28 between the reaction chamber 20 and the junction 50 or simply by closing of the valve 22. Closing of the valve 22 will immobilize fluids in the reaction arm 28 of the capillary due to the forces binding the fluid to the capillary wall. A valve 52 connected via lines 24 to vials 26, similar to the valve 22, is situated at the other end of the supply arm 48. The valve 52 may also be supplied with a vacuum pump 53 for use in evacuating the supply capillary during peptide or protein sequencing and waste 55 for draining fluids from the capillary 14. The supply arm 48 and the identification end 16 of the primary capillary 14 form a continuous capillary. Reagents or solvents delivered through valve 22 may be flushed to waste either through valve 52 or valve 17. Reagents and buffer solutions, used for example in electrophoresis, delivered through valve 52 may be flushed through valve 17 to waste.

Junction 50 may be made in several ways. It may use a commercially available T for attaching several fused silica capillaries together, in which T the capillary arms 28, 48 and 16 are inserted, the capillary arms all therefore comprising the continuous capillary 14. Or the capillary arms 28, 48 and 16 may be made of a unitary capillary with its arms fused together at the junction 50. Alternatively, the capillary 14 and the junction 50 can be formed by etching the capillary into a face of a solid block of inert material such as glass that abuts against a face of another block of inert material. Such a capillary can be formed by conventional micromachining techniques.

For electrophoresis separation of reaction product in the primary capillary 14, it may be desirable to convert reaction product into a form suitable for electrophoresis. In such a case, the supply arm 48 (FIG. 1), or the primary capillary 14 between the identification end 16 and the junction 50 (FIG. 2), may be provided with means to hold the reaction product in the supply capillary 14 for conversion. Such a means may be a thermocouple cooler 60 (Peltier device) made in accordance with the design shown for the heater 36 in FIG. 4, but with the polarity of the leads reversed to provide for cooling rather than heating. The cooler 60 may be used to freeze reaction product in the supply arm 48, where it may be subject to further reaction or conversion. The location of the thermocouple 60 therefore defines a conversion chamber 62 in the supply capillary 48 or in the primary capillary 14.

Figure 2:
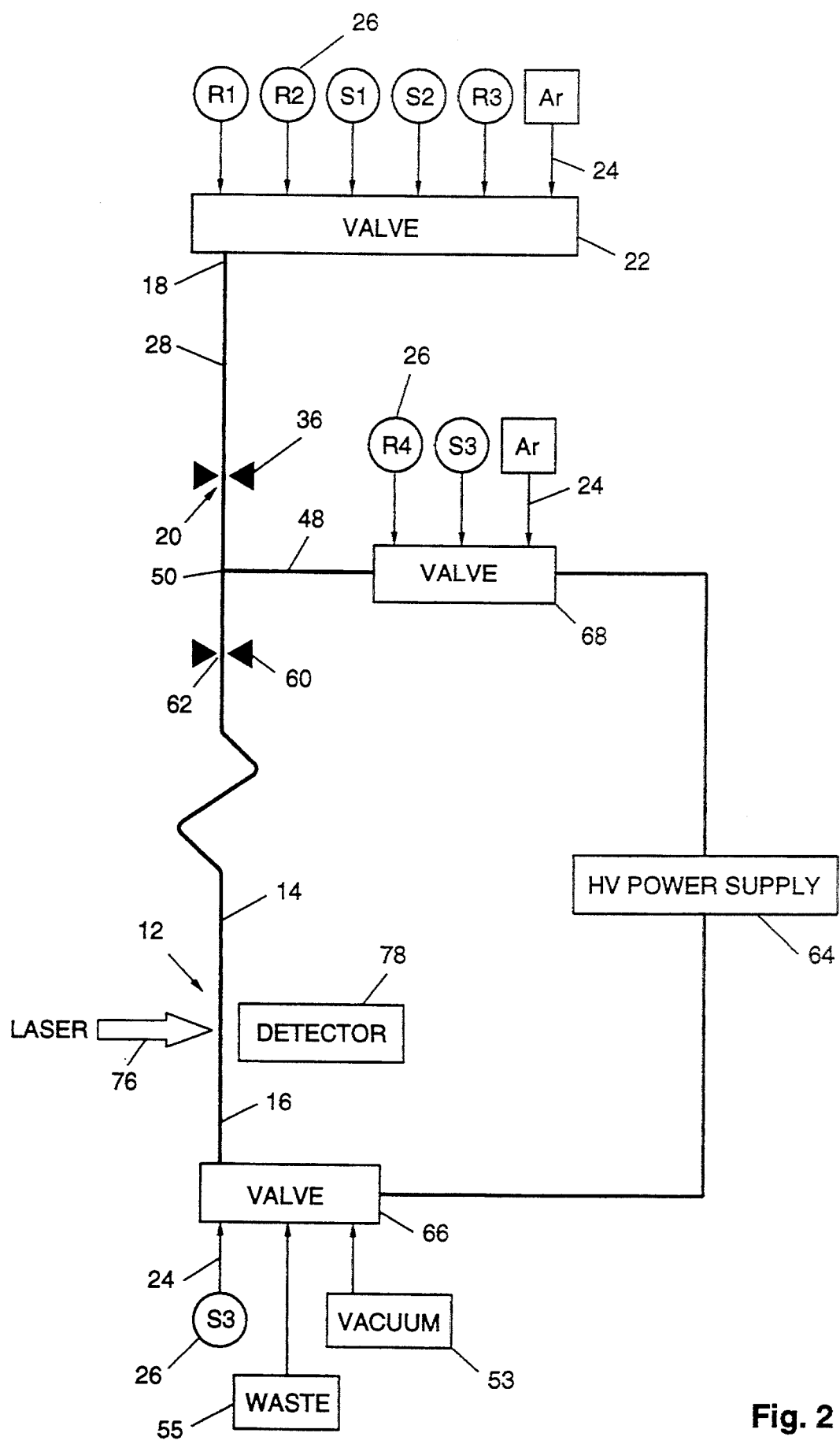
FIG. 2 is a schematic of another embodiment of a biochemical reactor and analyzer according to the invention.

In FIG. 2, which shows the conversion chamber in the primary capillary 14 between the junction 50 and the identification end 16, valve 66 is located at the identification end and valve 68 is located on the supply capillary 48. A vacuum pump 53 is attached to valve 66 for removing vapour from the conversion chamber 62 and valve 66 is also supplied with lines 24 and vials 26 for delivery of reagents and solvents to the supply capillary 48, while valve 68 is likewise supplied with lines 24 and vial 26.

Figure 3:
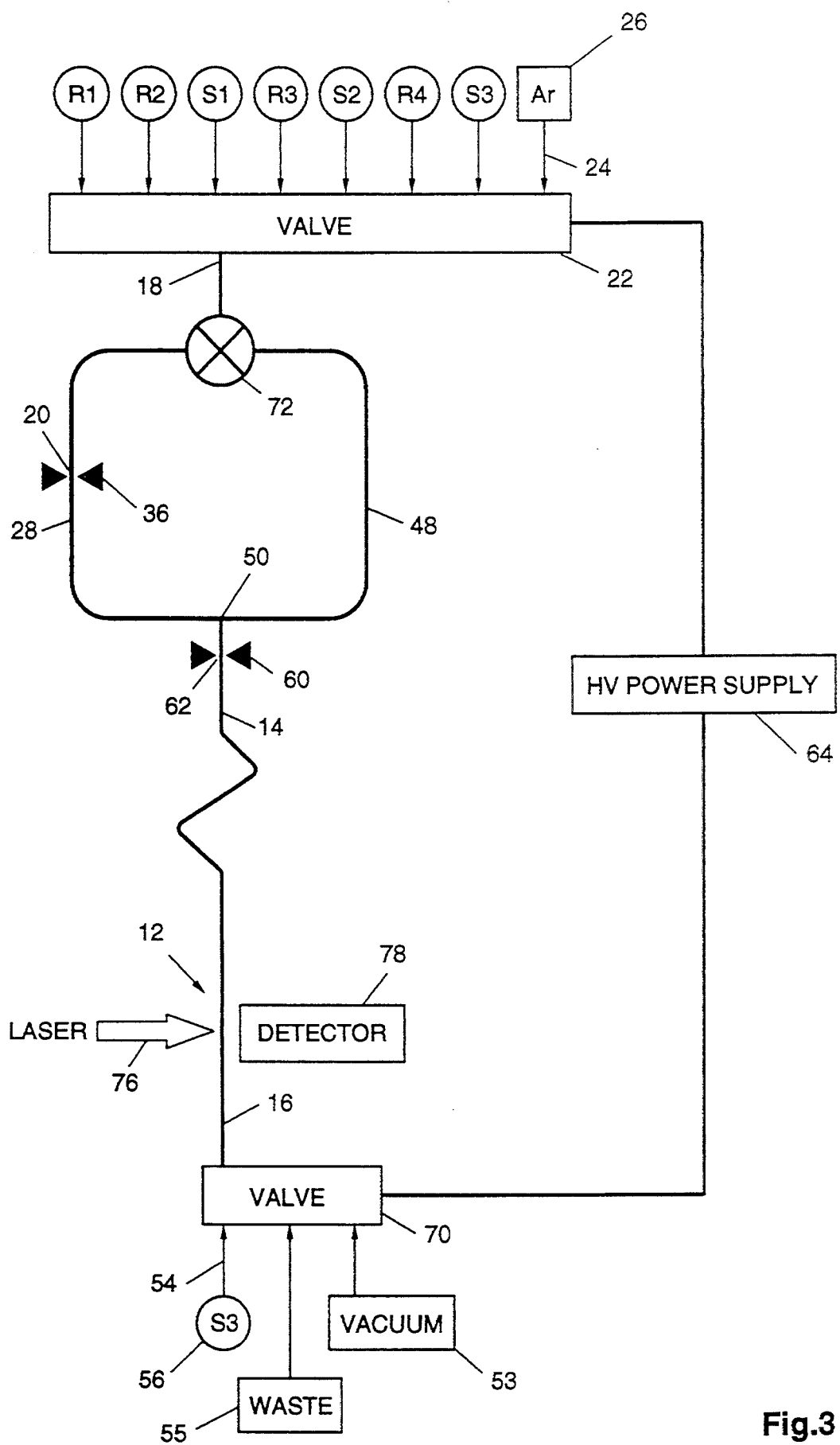
FIG. 3 is a schematic of another embodiment of a biochemical reactor and analyzer according to the invention.

For use in electrophoresis separation of the sample, a high voltage power supply 64 is connected to the valves 22 and 52 (FIG. 1), valves 22 and 66 (FIG. 2) or valves 22 and 70 (FIG. 3) at which electrodes (not shown) are applied to the electrophoresis medium in known manner. When the supply capillary 48 is not being used then the power supply may be connected to solution in the primary capillary via valve 22 as shown in FIG. 3. The length of capillary being used for electrophoresis must of course have electrophoretic length, that is, a length over which sufficient separation of the reaction product takes place so that it is identifiable.

A further embodiment of a peptide or protein sequencer is shown in FIG. 3. In this case, the supply capillary 48 connects as in FIG. 1 and 2 to the primary capillary 14 to form the junction 50, and also connects to the primary capillary 14 at reaction arm 28 between the reaction chamber 20 and valve 22 (same as the valve 22 shown in FIG. 1 but additional inlet lines 24 have been hooked up to the valve). A valve 70 is used for flushing and applying a vacuum to the identification end 16 of the primary capillary. A switching valve 72 at the junction of the capillary 48 and the reaction arm 28 permits fluids from valve 22 to be directed along either arm 28 or arm 48. Valve 22 therefore may be used to provide the same reagents as valve 52 in FIG. 1. By this means, one multi-position distribution valve may be omitted from the sequencer and replaced with a simple switching valve.

A more generalized reactor and analyzer are shown in FIG. 6. A capillary 14 extends continuously between a valve 22 and a valve 70, both of the multi-position distribution type described above as suitable for use as valve 22 in FIG. 1, with lines 24 and vials 26 respectively for providing reagent and solvents to the capillary 14, together with lines for application of a vacuum through pump 53 to the capillary 14, as well as for allowing waste to be removed from the capillary 14. The capillary 14 has a reaction end 18 and an identification end 16. The reaction end 18 includes a heater 36, such as is described in FIG. 4, and a holding means for holding a sample such as the reaction mats described in FIGS. 4 and 5. The holding means is located in a portion of the capillary 14 which thus forms a reaction chamber 20. An analyzer 12 formed for example of a laser 76 or other suitable light source and detector 78 is shown at the identification end, and the capillary 14 passes through the detection zone of the analyzer.

In general, following electrophoresis separation of a sample in the primary capillary 14, a laser 76 may be used to illuminate the sample and allow detection of the sample using a detector 78 using conventional electrophoresis methods such as those described in Jorgenson et al, *Capillary Zone Electrophoresis,* Science vol. 222, 266–272, 1983; Cheng et al, *Subattomole Amino Acid Analysis by Capillary Zone Electrophoresis and Laser Induced Fluorescence,* Science, vol. 242, pp. 562–564, 1988; Wu et al, *High Sensitivity Fluorescence Detector for Fluorescein Isothiocyanate Derivatives of Amino Acids Separated by Capillary Zone Electrophoresis,* Journal of Chromatography, 494, 1989, 141–155; Rohlicek et al, *Simple Apparatus for Capillary Zone Electrophoresis and its Application to Protein Analysis,* Journal of Chromatography, 494, 1989, 87–89; Yu et al, *Atttomole Amino Acid Determination by Capillary Zone Electrophoresis with Thermooptical Absorbence Detection,* Anal. Chem., 61, 1989, 37–40; Sweedler et al, *Fluorescence Detection in Capillary Zone Electrophoresis Using a Charged Coupled*

*Device with Time Delayed Integration*, Anal. chem. 63, 1991, 496–502; Monnig et al, *On-column Sample Gating for High Speed Capillary Zone Electrophoresis*, Anal. Chem., 63, 1991, 802–807; Deyl et al, *Design of a Variable Wavelength UV Absorption Detector for On-column Detection in Capillary Electrophoresis and Comparison of its Performance to a Fixed Wavelength UV-Absorption Detector*, Journal of Liquid Chromatography, 12(13), 1989, 2527–2561; Swerdlow et al, *Capillary Gel Electrophoresis for DNA Sequencing*, Journal of Chromatography, 516, 1990, 61–67; Waldron et al, *Capillary Zone Electrophoresis Separation and Laser Based Detection of Both Fluorescein Thiohydantoin and Dimethylaminoazobenzene Thiohydantoin Derivatives of Amino Acids*, Electrophoresis, 11, 1990, 777–780; Bruno et al, *Thermooptical Absorption Detection in 25 μmid Capillaries: Capillary Electrophoresis of Cansl-Amno Acids Mixtures*, Applied Spectroscopy, vol. 45, no. 3, 1990, 462–367; Swerdlow et al, *Three DNA Sequencing Methods Using Capillary Gel Electrophoresis and Laser Induced Fluorescence*, Anal. Chem., 63, 1991, 2835–2841; and Wu et al, *Capillary Zone Electrophoresis Separation and Laser-Induced Fluorescence Detection of Zeptomole Quantities of Fluorescein Thiohydantoin Derivatives of Amino Acids*, Talanta, vol. 39, no. 2, 173–178, 1992. The detector 78 and laser 76 together form an analyzer. Various analyzers may be used in conjunction with the reactor and analyzer combination described here.

Figure 7:
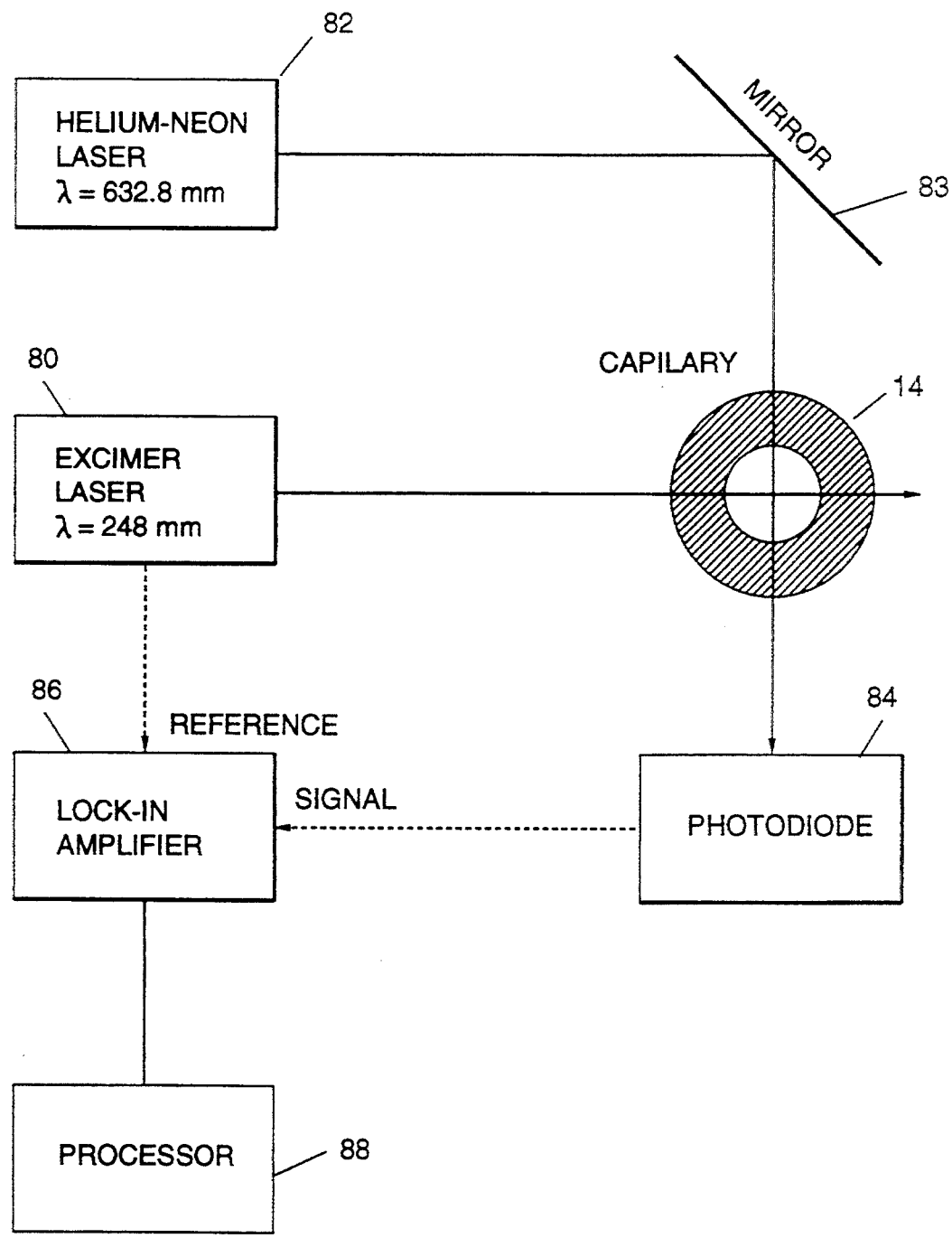
FIG. 7 is a schematic of an analyzer for use with any of the reactors shown in FIGS. 1, 2, 3, 6, 9 or 10.

A sample analyzer 12 or identification means is shown in FIG. 7. A portion of the identification end 16 of capillary 14 is shown in cross-section. The capillary 14 (50 μm ID, 190 μm OD) is illuminated with a laser 80 that is selected for absorption of its output by the sample carried by electrophoretic medium within the capillary 14, such as a 5 mW average power 10-μJ pulse energy KrF excimer waveguide laser (Potomac Photonics Model GX-500) operating at λ=248 nm, 610 Hz pulse repetition rate and 50 ns pulse width. The laser beam is focused with a 15 mm focal length quartz biconvex lens at right angles to the capillary, the location of the laser beam thus defining a detection zone of the analyzer through which the capillary passes. If the capillary 14 has a polyimide coating, it should be removed as for example by burning with a gentle flame. The output beam of a second laser 82, such as a 3 mW helium-neon laser (Melles Griot Model 05-LHP-151), is directed at right angles to both the capillary 14 and the beam from the laser 80, and focused with a 7× lens. For convenience, the beam may be reflected one or more times with mirrors, such as mirror 83. A transducer 84, for example a 1 mm² silicon photodiode, is located in the beam path of the laser 82 at the other side of the capillary 14 from the laser 82, about 30 cm from the capillary. An electric signal from the transducer 84 is conditioned with a current to voltage converter (1 M ohm feedback resistor in parallel with a 47 pF capacitor) and supplied to an amplifier 86. The exemplary amplifier is a two-phase lock-in amplifier (Ithaco Model 3961) phase referenced to the excimer laser pulse repetition rate. Data from the lock-in amplifier 86 is supplied to a processor 88 (for example a personal computer). The data may be processed by any of several known methods, as for example using Matlab software to convolute the data with a gaussian filter.

Sample amino acids in the buffer solution in the capillary 14 are selectively excited by the radiation from the excimer laser and relaxation from the excited state heats the buffer solution, resulting in a change in the index of refraction of the solution and the consequent bending of the laser beam from the helium neon laser 82. The deflection of the laser beam is recorded as a change in intensity of light detected by transducer 84.

The data is in the form of electromagnetic signals. The magnitude of the signals depends on the amount of light detected by the transducer, which in turn depends on the index of refraction of the electrophoretic medium, which depends on the degree to which it is heated, which in turn depends on the amount of amino acid with light absorption characteristics in the electrophoretic medium. Hence the data is representative of the amount of amino acid in the electrophoretic medium at a particular time.

Figure 8:
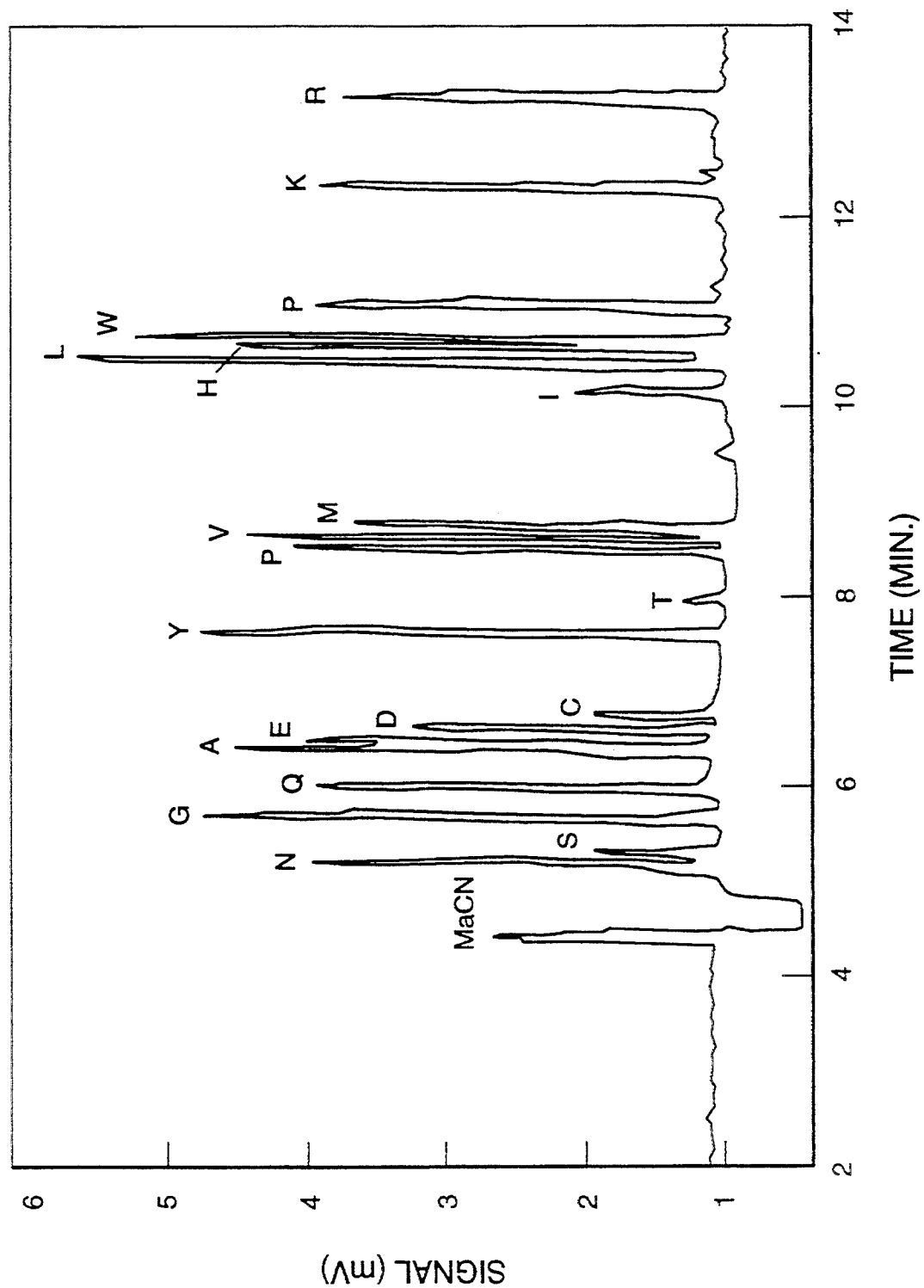
FIG. 8 is a graph showing results of use of the analyzer in FIG. 7.

Results of using the apparatus shown in FIG. 7 for the detection of PTH-amino acids are shown in FIG. 8. In this case, the length of capillary 14 before the detector was 34 cm. A voltage of 8 kV was placed across the capillary. A 12.5 mM pH 7.0 borate/phosphate buffer containing 35 mM sodium dodecyl sulfate was used for electrophoresis medium. Electrokinetic injection of 5 s at 500 V was used. Stock solutions of $10^{-2}$ concentration of the amino acids alanine (A), arginine (R), asparagine (N), aspattic acid (D), cysteic acid (C), serine (S), glutamine (Q), glutamic acid (E), glycine (G), histidine (H), isoleucine (I), leucine (L), PTH-PTC lysine (K), methionine (M), phenylalanine (F), proline (P), threonine (T), tyrosine (Y), tryptophan (W) and valine (V) were prepared by dissolving each amino acid in a 50% acetonitrile and 50% mM phosphate/borate buffer. Mixtures of amino acids were prepared by pipetting 10 μL aliquots into 1.5 mL of 12.5 mM pH 7.0 borate/phosphate buffer that contained 35 mM sodium dodecyl sulfate. The peaks shown in FIG. 8 are identified according to the letter in parenthesis listed after each amino acid noted above. A 1.1 mV baseline signal is due to absorbance of the excimer laser beam by trace impurities in the separation buffer. The disturbance at 4.5 min. is due to the elution of trace amounts of acetonitrile, added to the analyte to effect dissolution. The arrival time of a specific peak from the analysis of an unknown amino acid may be compared with the arrival times of known amino acids shown in the graph of FIG. 8 and thus identify the amino acid.

The electrophoretic separation was by micellar electrophoresis, as described in Otsuka et al, *Electrokinetic Chromatography with Micellar Solutions Separation of Phenylthiohydantoin-Amino Acids*, 2. Chromatogr. 332, 1985, p. 219–226. Micellar electrophoresis is particularly useful when the amino acid residue is not charged. The buffer fluid have moves in one direction in the electric field established by the high voltage source 64, while micelles in the buffer fluid have electrophoretic mobility in an opposite direction. The amino acid residue is partitioned in and out of the micelies, and during partitioning is carried with the flow of buffer. Each amino acid has a different partition coefficient which governs the length of time it remains in the micelle. Hence, the length of time the amino acid takes to travel along the capillary is an indication of the type of amino acid. The results shown in FIG. 8 were not obtained using the apparatus of FIGS. 1, 2 or 3 but are believed representative of results that could be obtained by the repetitive sequencing of a peptide or protein using the apparatus of any of FIG. 1, 2 or 3.

Other analyzers may be used. When FITC is used as the degradation coupling agent in the Edman reaction, the analyzer may use capillary zone electrophoresis and direct identification of FTC (fluorescein thiocarbamyl) following well known techniques as for example described by Wu, S. et al, *Capillary Zone Electrophoresis Separation and Laser Induced Fluorescence Detection of Zeptomole Quantities of Fluorescein Thiohydantoin Derivatives of Amino Acids*, Talanta, Vol. 39, No. 2, pp. 173–178, February 1992. The fluorescence detector may use a sheath flow cuvette design as described in Cheng et al, *Subattomole Amino Acid Analysis by Capillary Zone Electrophoresis and Laser Induced Fluorescence*, Science, vo. 242, pp. 562–564, October 1988.

The analyzer 12 may also use high performance liquid chromatography, or other types of liquid chromatography, such as described in Kettler et al, *Pulsed-Laser Photothermal Refraction Detection in Capillary Liquid Chromatography*, Anal. Chem. 1987, 59, 1733–1736, or mass spectrometry.

If a detector is used which requires the consumption of the reaction product by the analyzer, such as in electrophoresis using a sheath flow cuvette or a mass spectrometer, then the reaction product and the solution carrying it must be taken out of the capillary 14 into the analyzer.

Figure 9:
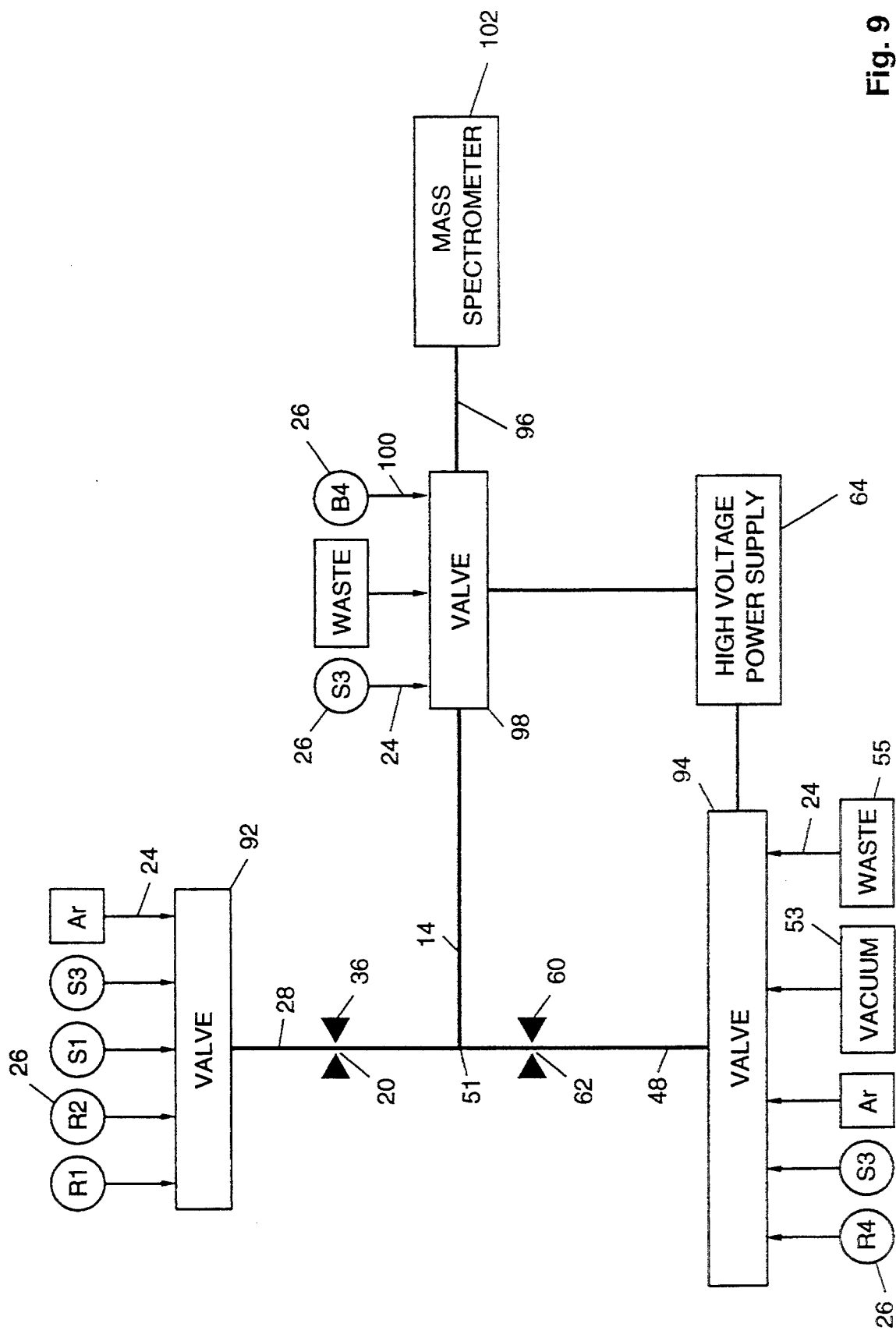
FIG. 9 is a schematic of an embodiment of a biochemical reactor and analyzer according to the invention in which the analyzer is a mass spectrometer.
Figure 10:
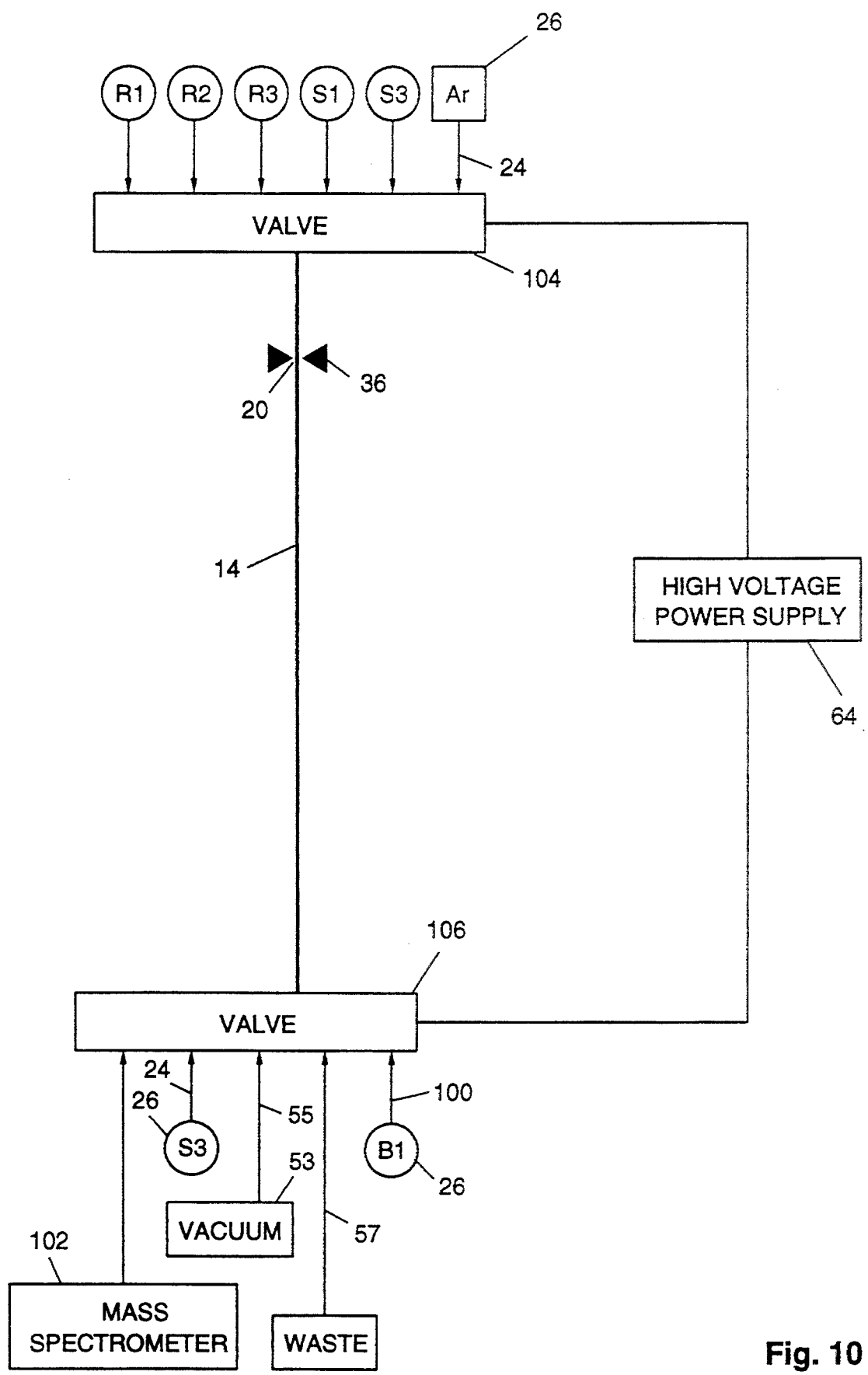
FIG. 10 is a schematic of another embodiment of a biochemical reactor and analyzer according to the invention in which the analyzer is a mass spectrometer.

An example of such a device is shown in FIGS. 9 and 10. In FIG. 9, valve 92, with inlet lines 24 and vials 26, has its common outlet connected to a reaction arm 28 of a capillary 14. A thermocouple 36 is placed about a portion of the arm 28 and defines a reaction chamber 20 in the capillary arm 28. Means to immobilize a sample to be reacted is located in the reaction chamber 20 for example as shown in FIGS. 4 or 5. A supply capillary arm 48 leads from junction 51 to valve 94, with lines 24 and vials 26. On the supply capillary 48 is a thermocouple 60 defining a conversion chamber 62 in the supply capillary. At an identification end 96 of the capillary 14, a valve 98 is located, with the end 96 terminating in the ionization chamber of a mass spectrometer 102. The mass spectrometer may be a triple quadrupole mass spectrometer sold by Sciex Division of MDS Health Group Limited, of Thornhill, Ontario, Canada, under its trademark TAGA 60000E. Ionization of reaction product from the reaction chamber may be enhanced using the techniques described in U.S. Pat. No. 4,935,624 to Henion et al. The overall structure and operation of the apparatus shown in FIG. 9 is similar to the operation of the apparatus shown in FIG. 1, except that a line 100 for carrying mass spectrometer buffer liquid or gas from a vial 26 is provided on the valve 98 that can be added to the reaction product in capillary 14 for delivery into the mass spectrometer 102 for analysis.

FIG. 10 shows a device similar to the device of FIG. 6, used for example for amino acid analysis and N-terminal amino acid identification. As in FIG. 6, there is no means to isolate the reaction chamber during electrophoresis with the consequence that application of the buffer will hydrolize any truncated peptide or protein and prevent further analysis, apart from a first amino acid that has been cleaved from the protein or peptide. Capillary 14 extends between valve 104 and valve 106, each with lines 24 and vials 26 and has a thermocouple 36 (or other heater) at a portion of the capillary defining a reaction chamber 20. A high voltage power supply 64 is placed across the valves 104 and 106 with electrodes connectable to buffer solution supplied through the line at vials indicated by S3. Vacuum is provided from pump 53 through line 55 and waste through line 57. Sheath buffer or gas for mass spectrometry is provided through line 100. The capillary 14 continues through the valve 106 (through internal capillary lines within the valve) to mass spectrometer 102, similar to the mass spectrometer shown in FIG. 9.

Figure 11:
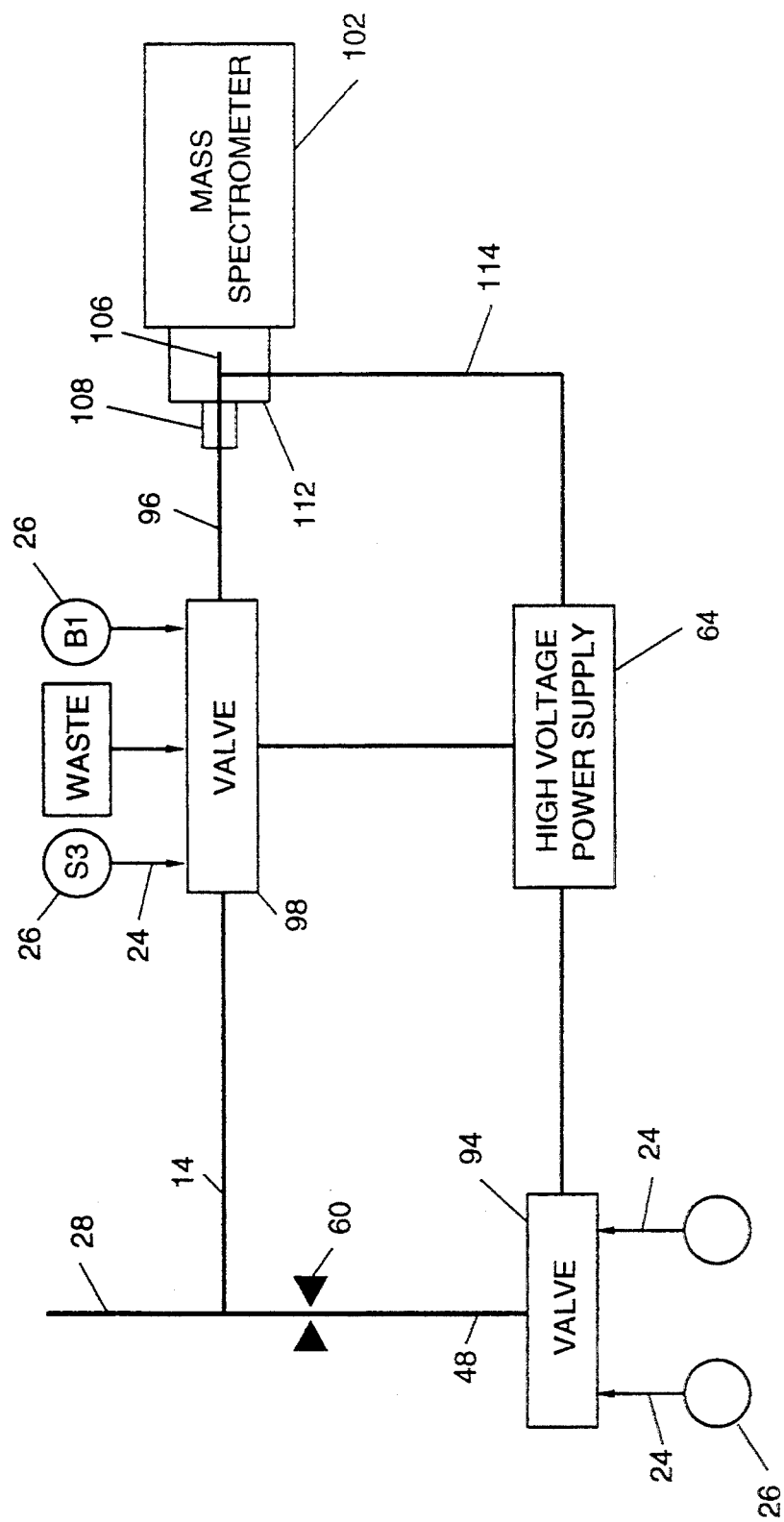
FIG. 11 is a schematic showing a portion of an embodiment of the invention for use in association with a mass spectrometer electrospray device as the analyzer.

If an electrospray device is used for the delivery of reaction product to the mass analyzer, then a slightly different structure must be used. In FIG. 11 there is shown a modification of the design shown in FIG. 9. The design is the same except that an electrospray device 108 is shown on the mass spectrometer, such as is described in Henion et al, U.S. Pat. No. 4,935,624. The tip 110 of the capillary 14 extends into the mass spectrometer ionization chamber 112. The tip 110 of the capillary 14 will in this case be conducting, and typically the capillary in this portion will be made of stainless steel. A lead 114 from the high voltage source 64 connects to the tip 110 of the capillary 14 thus establishing an electric potential through the electrophoretic medium to valve 94. Separation of amino acids takes place in the capillary 14, while analysis takes place in the mass spectrometer 102.

Figure 12:
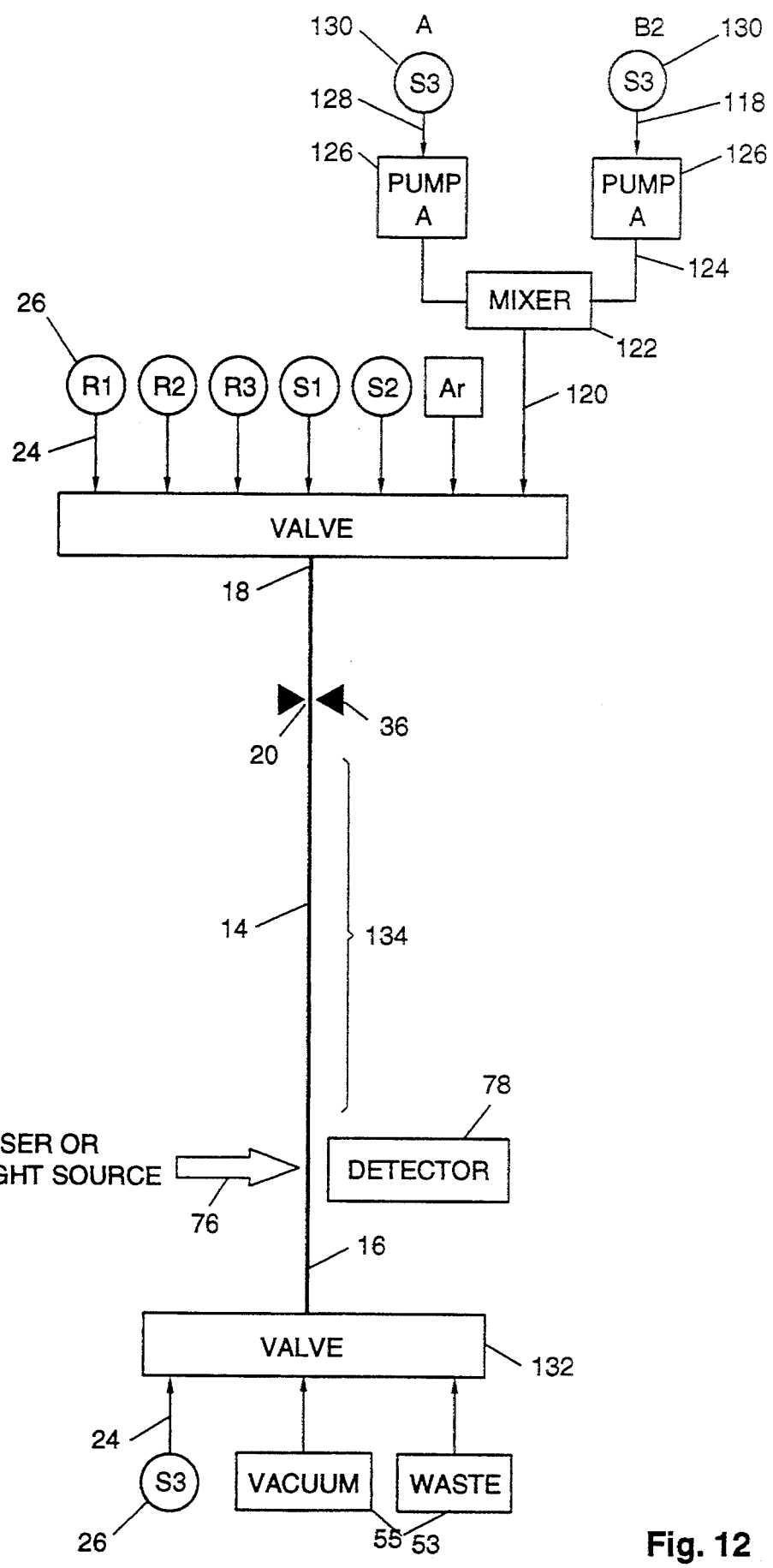
FIG. 12 is a schematic showing an embodiment of the invention in which the analyzer uses liquid chromatography for analysis.

FIG. 12 shows a further embodiment of the invention in which liquid chromatography is used for analysis. Valve 22 has its common port connected to a reactor end 18 of capillary 14. The valve 22 has various of its inlet ports connected to lines 24 leading to vials 26 containing reagents (R) or solvents (S). One inlet port is connected to a line 120 leading to a gradient mixer 122, which is supplied aqueous buffer (A) and an organic modifier (B2) from vials 130 through lines 128 and pumps 126. Since liquid chromatography does not use electrophoresis, no high voltage source is required. If isochratic chromatography is used, only one pump is required. The reaction end 18 of the capillary 14 includes a thermocouple 36 and reaction chamber 20, like the reaction chamber 20 shown in FIG. 4 or 5. The capillary 14 passes through the detection zone of an analyzer formed by laser or equivalent light source. 76 and detector 78. At least the portion 134 of the capillary 14 between the reaction chamber 20 and the detection zone of the analyzer is filled with liquid chromatographic packing material, such as coated silica beads. The capillary should have an inner diameter suitable for receiving the packing material, such as 250 μm. The other end 16 of the capillary 14 terminates in a valve 132, having inlet ports connected via line 24 to vial 26 and to a vacuum pump 53 and waste 55. FIG. 12 shows the set up for liquid chromatography when used for amino acid analysis or other analysis in which hydrolysis of the sample after a first reaction step is not a concern. If a peptide is sequentially reacted in the reaction chamber, as for example in Edman degradation, then a supply or bypass capillary such as the capillary shown in FIGS. 1, 2, 3 or 9 would be required with suitable modifications to the valves. In addition, rather than a light source 76 and detector 78, a mass spectrometer as shown in FIG. 10 could be attached to an inlet port of valve 132.

The manner of operation of the various apparatus referred to in FIGS. 1, 2 or 3 is now described. It will be appreciated that the basic chemistry is known in the art so that the details of the chemistry will not be described. In the case of each of the apparatus shown, the vials 26 have been labelled according to their use in amino acid identification, including peptide or protein sequencing in the case of the apparatus described in FIGS. 1, 2 and 3. The following table indicates the use of the vials:

| Label | Use |
|---|---|
| R1 | Coupling agent, for example PITC |
| R2 | TMA (trimethylamine) |
| S1 | Wash fluid, eg Ethyl acetate |
| S2 | Solvent, for example benzene |
| S3 | Electrophoresis medium (buffer soln) |
| B1 | Mass spectrometer buffer |
| R3 | Anhydrous acid, for example TFA |
| R4 | Aqueous acid, for example TFA |
| Ar | Source of inert gas, for example argon |
| Vacuum | Indicates a pump for evacuating the capillary. |
| Waste | A drain for removing fluids from the capillary |

Referring to FIGS. 1, 2 or 3, firstly, the sample peptide or protein is loaded onto the reaction mat 32 and the reaction chamber heated to about 60° C. Using valve 22 for input and valves 52, 66 and 70 for waste, peptide degradation coupling agent, for example PITC, is then introduced into the reaction arm 28 with heptane and the reaction mat dried under argon. In the case of the apparatus shown in FIG. 3, the switch valve 72 is switched for the duration of coupling and cleavage to isolate the supply capillary 48 from the primary capillary 14 during coupling and cleavage. TMA is then introduced to reaction arm 28 to promote formation of coupled peptide. Unwanted material may be flushed out with ethyl acetate input via valve 22 to waste through valves 52 (FIG. 1), 66 (FIG. 2) or 70 (FIG. 3). Anhydrous acid (TFA), either as a pulsed liquid or saturated vapour in argon, is introduced to reaction arm 28 and the reaction chamber 20 where it cleaves the amino acid residue from the coupled peptide to produce amino acid residue and leaving a peptide that has been truncated by one amino acid. Throughout these steps, valve 17 in FIG. 1 is held closed. A like process is used for the apparatus of FIGS. 2 and 3, although in the case of FIG. 3, valve 17 is not present.

Once the amino acid residue (reaction product) has been produced, it is extracted from the reaction mat 32 using a solvent such as benzene, with a freezing point around 0° C., introduced via valve 22 through the reaction arm 28. The benzene, with some of the amino acid residue dissolved in it, is transported into the supply capillary 48 or the identification arm 16 in the case of the apparatus of FIGS. 2 or 3 where it is frozen into place using the thermocouple 60. A vacuum imposed on the supply capillary 48 through one of valve 52 (FIG. 1), 66 (FIG. 2) or 70 (FIG. 3) may then be used to sublime the solvent, leaving the amino acid residue frozen into the conversion chamber 62. The conversion chamber may then be raised to room temperature (by reversing the polarity of the power applied to the thermocouple 60) and a small slug of aqueous acid is introduced through valve 52 to valve 17 (FIG. 1), valve 68 to valve 53 (FIG. 2) or valve 22 to valve 70 (FIG. 3) to convert the ATZ amino acid residue to PTH amino acid residue (second reaction product) in the conversion chamber. During conversion, the reaction chamber 20 must be isolated to avoid hydrolysis of the truncated peptide, such as by closing valve 22 (and closing off the reaction chamber using valve 72 in the apparatus of FIG. 3). The conversion chamber 62 is again frozen using the thermocouple 60 and the aqueous acid removed by vacuum through one of valves 52, 66 or 70. Again the conversion chamber is brought to room temperature using the thermocouple 60.

The next step is identification or analysis. The supply capillary 48 and identification arm 16 of the capillary 14 are filled with aqueous pH 7 buffer or other capillary electrophoresis buffer from valve 22 through valve 17 (FIG. 1), valve 68 to valve 66 (FIG. 2) or valve 22 to valve 70 (FIG. 3, after switching of the valve 72 to isolate the reaction chamber 20). Valve 52, valve 68 or valve 22 is then switched to a separation buffer containing acetonitrile, sodium dodecyl sulfate and 20 mM pH 7 aqueous buffer. Potential is then applied across the conversion chamber from valve 52 through valve 17 (FIG. 1), valve 68 to 66 (FIG. 2) or valve 22 to valve 70 with one valve held at an electrophoretic potential such as ±8 kV to induce electrophoresis separation of amino acids in the capillary with the other valve grounded. The distance between the conversion chamber and the analyzer 12 should be an electrophoretic length in which sufficient separation of the amino acid residue will take place to allow analysis. The amino acid is identified using one of various analyzers at the identification end 16.

A program for the apparatus shown in FIG. 1 is set out at the end of this disclosure in Tables 2, 3, 4 and 5. Table 2 shows the function of each of the valve positions for the valves of FIG. 1 (Valve A corresponds to valve 22, valve B to valve 52 and valve C to valve 17). Table 3 shows the time sequence of steps in the program. Peltier1 is heater 36. Peltier2 is thermocouple 60. Spellman HV is the high voltage source 64. CZE means capillary zone electrophoresis. Table 4 shows the inside and outside diameters and the length of the capillary tubing hooked up to the various valve positions or if Teflon tubing is used instead of capillary tubes. The valves may be automatically programmed for these steps if desired using hardware provided by the manufacturer. For the apparatus of FIG. 6, a like process is followed. However, in the case of amino acid analysis or N-terminal amino acid analysis or similar such analyses, where isolation of the peptide or protein or other sample is not required, the conversion step is not required and an electrophoretic potential can be applied across the reaction chamber after formation of the reaction product and filling of the capillary with an appropriate buffer. Separation then occurs as with conventional electrophoresis, followed by analysis at the analyzer. In the case of the apparatus shown in FIGS. 9, 10, 11 and 12, like steps of the Edman degradation reaction may be carried out. The method steps for the apparatus of FIGS. 9 and 11 are analogous to those of FIG. 2, and the method steps of FIGS. 10 and 12 are analogous to those of FIG. 6, with the exception that mass spectrometry buffer must be added to the solution through line 100 following electrophoresis for use of the apparatus of FIG. 10 and liquid chromatographic identification using the aqueous buffer A and organic modifier B2 in conventional manner must be carried out for use of the apparatus of FIG. 12 following degradation. That is, for liquid chromatography, after amino acid residue has been produced by the Edman degradation reaction, the chamber is dried, leaving only amino acid residue in the reaction chamber. Then aqueous buffer A and organic modifier B2 is pumped through the gradient mixer 122 into capillary 14, with a gradually increasing ratio of modifier to buffer. Amino acids attach to the liquid chromatographic packing material in the capillary 14 and as the modifier to buffer ratio is increased, amino acids selectively detach from the packing material and pass through the detection zone of the analyzer whence they can be identified in known manner.

The following is a comparison of an embodiment of the present invention with a commercial sequencer following the Hewick apparatus design:

TABLE 1

| ITEM | COMMERCIAL SEQUENCER | PRESENT SEQUENCER |
|---|---|---|
| reaction chamber volume | 150 μL | 0.2 μL |
| glass-fibre filter area | 450 mm² | 0.5 mm² |
| max. sample volume | 30 μL | 0.04 μL |
| gas reagent flow rate | 3 mL/min. | 0.05 mL/min |
| liquid reagent flow rate | 0.5 mL/min. | abt 0.004 mL/min.* |
| cycle duration | 45–60 min | 20–30 min |
| minimum amount sequenceable | 1 picomole | 1 femtomole |

*(flow rates differ slightly depending on viscosity of solvent and tubing I.D.)

The reaction chamber volume defined in Table 2 is the volume in which the raction mat sits.

A person skilled in the art could make immaterial modifications to the invention described and claimed in this patent without departing from the essence of the invention. Thermocouples need not be used for heating (thermocouple 36) nor for heating and cooling (thermocouple 60), rather other heating and cooling techniques could be used. For holding the reaction product in the conversion chamber, a packed bed of chromatographic material, such as silica beads, could be fixed in the capillary using such techniques as sintering. A like technique could be used for immobilizing the sample in the reaction chamber, with Polybrene applied to the bed of beads. The apparatus is not limited to use for analysis of samples in solution. The apparatus may also be used for solid phase sequencing.

While multi-position valves have been described as being used for the valves 22, 53 etc, it is possible to use miniature syringe pumps for the fluid flow control means, and various types of multi-position valves may be used. The capillary 14 may be a silica tube made of one or more members or etched in a glass block for example. For the carrying out of some reactions, for example the Edman degradation reaction, a valve with randomnly accessible ports may be preferred, rather than a valve in which the valves must be used sequentially. For carrying out the Edman degradation reaction using the degradation agents dimethylaminoazobenzene isothiocyanate (DABITC) or fluorescein isothiocyanate (FITC), or with combinations of PITC with FITC or DABITC, additional ports are required beyond the ports described in FIG. 1 for example to handle the DABITC or FITC. If necessary, an additional valve may be used, also connected to the reaction end of capillary 14. The program outlined in Table 3 would be used, modified for the particular degradation agent used.

TABLE 2

| Valve A positions | Valve B positions | Valve C positions |
|---|---|---|
| 1. 12% TMA | 1. waste | 1. plug |
| 2. PITC | 2. vacuum | 2. waste |
| 3. Ar | 3. plug | 3. plug |
| 4. 12% TMA | 4. Ar | 4. waste |
| 5. Ar | 5. 25% TFA | 5. CZE buffer (14 psi) |
| 6. Ethyl Acetate | 6. Ar | 6. CZE buffer + HV |
| 7. Ar | 7. plug | 7. waste |
| 8. TFA vapour | 8. vacuum | 8. vacuum |
| 9. Ar | 9. plug | 9. waste |
| 10. Benzene | 10. CZE buffer (3.5 psi) | 10. plug |
| 11. Ar | 11. CZE buffer (no Ar) | 11. plug |
| 12. plug | 12. Ar (14 psi) | 12. plug |

TABLE 3

| Valve A | Valve B | Valve C | Notes |
|---|---|---|---|
| — | — | — | Peltier1 on, heat (65 C.) 1.40 v |
| 1. 12% TMA | 1. waste | 1. plug | Peltier1 on, heat (65 C.) 1.40 v (0:40 min) |
| 2. PITC | " | " | Peltier1 on, heat (65 C.) 1.40 v (0:03 min) |
| 3. Ar | " | " | Peltier1 on, heat (65 C.) 1.40 v (2:00 min) |
| 4. 12% TMA | " | " | Peltier1 on, heat (65 C.) 1.40 v (7:30 min) |
| 5. Ar | " | " | Peltier1 on, heat (65 C.) 1.40 v (2:00 min) |
| " | " | " | Peltier1 off (0:06 min) |
| 6. Ethyl Acetate | " | " | " |
| 7. Ar | " | " | (3:00 min) |
| " | " | " | Peltier1 on, heat (48 C.) 0.94 v |
| 8. TFA vapour | " | " | Peltier1 on, heat (48 C.) 0.94 v (6:00 min) |
| " | " | " | Peltier1 off |
| 9. Ar | " | " | (2:00 min) |
| " | " | " | Peltier2 on, freeze (−10 C.) 1.45 v |
| 10. Benzene | " | " | Peltier2 on, freeze (−10 C.) 1.45 v (0:10 min) |
| 11. Ar (75/360 um) | " | " | Peltier2 on, freeze (−10 C.) 1.45 v (1:00 min to push benzene) |
| 12. plug | " | " | Peltier2 on, freeze (−10 C.) 1.45 v (1:00 min to push benzene) |
| | 2. vacuum | " | Peltier2 on, freeze (−10 C.) 1.45 v (3:00 min to remove benzene) |
| " | 3. plug | " | Peltier2 on, freeze (−10 C.) 1.45 v (3:00 min to remove benzene) |
| " | 4. Ar | " | Peltier2 on, freeze (−10 C.) 1.45 v (3:00 min to remove benzene) |
| " | " | 2. waste | Peltier2 on, freeze (−10 C.) 1.45 v (1:00 min to dry) |
| " | 5. 25% TFA | " | Peltier2 on, freeze (−10 C.) 1.45 v |

TABLE 3-continued

| Valve A | Valve B | Valve C | Notes |
|---|---|---|---|
| " | 6. Ar (75/360 um) | " | (0:05 min)<br>Peltier2 on, freeze (−10 C.) 1.45 v<br>(0:08 min to push TFA thru) |
| " | 7. plug | " | Peltier2 on, freeze (−10 C.) 1.45 v<br>(0:08 min to push TFA thru) |
| " | " | 3. plug | Peltier2 on, freeze (−10 C.) 1.45 v<br>(0:08 min to push TFA thru) |
| " | " | " | Peltier2, heat (65 C., 10:00 min) |
| " | " | " | Peltier2 on, freeze (−10 C.) |
| " | 8. vacuum | " | Peltier2 on, freeze (−10 C.)<br>(4:00 min to remove aq TFA) |
| " | 9. plug | " | Peltier2 on, freeze (−10 C.)<br>(4:00 min to remove aq TFA) |
| " | 10. CZE buffer | " | Peltier2 on, freeze (−10 C.)<br>(0:05 min, fill to Peltier 2) |
| " | " | 4. waste | |
| " | " | 5. CZE buffer (14 psi) | Peltier2 on, freeze (−10 C.)<br>(2:25 min, fill to Peltier 2) |
| " | " | " | Peltier 2 off |
| " | " | 6. CZE buffer + HV | |
| " | 11. CZE buffer, no | " | |
| " | " | " | Spellman HVon, start CZE prog. |
| " | 12. plug | " | |
| " | " | 7. vacuum | (4:00 min to remove buffer) |
| " | " | 8. Ar (14 psi) | |
| " | 1. waste | " | (2:00 min to dry) |
| " | " | 9. plug | |
| " | " | 10. plug | |
| " | " | 11. plug | |
| " | " | 12. plug | |
| " | " | 1. plug | 2nd cycle starts |

TABLE 4

| Valve A positions | Valve B positions | | Valve C positions | |
|---|---|---|---|---|
| 1. 12% TMA | 75/360 × 60 cm | 1. waste | 98/230 × 30 cm | 1. plug |
| 2. PITC | 250/340 × 55 cm | 2. vacuum | teflon tubing | 2. waste | 75/360 × 25 cm |
| 3. Ar | 75/360 × 60 cm | 3. plug | | 3. plug |
| 4. 12% TMA | 75/360 × 60 cm | 4. Ar | teflon tubing | 4. waste | 75/360 × 25 cm |
| 5. Ar | 250/340 × 58 cm | 5. 25% TFA | 250/340 × 40 cm | 5. CZE buffer (14 psi) | 250/340 × 30 cm |
| 6. Ethyl Acetate | 250/340 × 50 cm | 6. Ar | 75/360 × 40 cm | 6. CZE buffer + HV electrode | 250/340 × 25 cm |
| 7. Ar | 75/360 × 50 cm | 7. plug | | 7. waste | 250/340 × 20 cm |
| 8. TFA vapour | 75/360 × 53 cm | 8. vacuum | teflon tubing | 8. vacuum | teflon tubing |
| 9. Ar | 250/340 × 50 cm | 9. plug | | 9. waste | 250/340 × 20 cm |
| 10. Benzene | 250/340 × 47 cm | 10. CZE buffer (3.5 psi) | 250/340 × 40 cm | 10. plug |
| 11. Ar | 75/360 × 50 cm | 11. CZE buffer (no Ar) | 250/340 × 40 cm | 11. plug |
| 12. plug | | 12. Ar (14 psi) | teflon tubing | 12. plug |

The embodiments of the invention in which an exclusive property or privilege is claimed are defined as follows:

1. A combined reactor and analyzer for reacting and analyzing a sample, the reactor and analyzer comprising:
   (a) a continuous capillary including:
      (i) a primary capillary portion having a reaction end and an identification end, first fluid flow control means being disposed at the reaction end and second fluid flow control means being disposed at the identification end; and
      (ii) a supply capillary portion having a first end and a second end, the first end being connected to the primary capillary portion between the reaction end and the identification end to form a junction, and the second end having third fluid flow control means for supplying fluid to the supply capillary portion and to the identification end of the primary capillary portion;
   (b) sample holding means at a first selected portion of the reaction end of the primary capillary portion for selectively holding a sample within the reaction end of the primary capillary portion for reaction to form a reaction product, the first selected portion defining a reaction chamber; and
   (c) identification means at the identification end for identifying the reaction product within said primary capillary portion.

2. The combined reactor and analyzer of claim 1 further including:
   reaction product holding means at a second selected portion of the supply capillary portion or the primary capillary portion between the third fluid flow control means and the identification end for holding the reaction product for further reaction.

3. The combined reactor and analyzer of claim 2 in which the identification means includes:
   a laser for irradiating the reaction product in the primary capillary portion;
   means for detecting fluorescence from irradiated reaction product; and
   means for establishing an electric field in electrophoretic medium in the supply capillary portion and primary capillary portion along an electrophoretic length of the supply capillary portion and the primary capillary portion while isolating the reaction chamber from the electrophoretic medium.

4. The combined reactor and analyzer of claim 2 in which the identification means includes:
- means for electrophoretically separating the reaction product by passage through an electrophoretic medium;
- a first laser for exciting the reacted sample in a portion of the electrophoretic medium with laser light that is selectively absorbed by the reaction product;
- a second laser for directing a beam of light at the reacted sample; and
- means for detecting deflection of the beam of light due to heating of the electrophoretic medium following excitation of the reaction product.

5. The combined reactor and analyzer of claim 2 further including a valve across the primary capillary portion between the reaction chamber and the junction between the supply capillary portion and the primary capillary portion, whereby isolation of the reaction chamber from the identification end of the primary capillary portion may be ensured.

6. The combined reactor and analyzer of claim 2 in which the reaction product holding means is formed from a cooling device disposed about the supply capillary portion.

7. The combined reactor and analyzer of claim 2 in which the reaction product holding means is formed from a cooling device disposed about one of the supply capillary portion and the primary capillary portion.

8. The combined reactor and analyzer of claim 2 in which the primary capillary portion has an inside diameter of less then 530 $\mu$m.

9. The combined reactor and analyzer of claim 2 in which:
- the reaction product holding means is located at the supply capillary portion between the junction and the third fluid flow control means.

10. The combined reactor and analyzer of claim 9 in which the identification means includes:
- a laser for irradiating the reaction product in the primary capillary portion;
- means for detecting fluorescence from irradiated reaction product; and
- means for establishing an electric field in electrophoretic medium in the supply capillary portion and primary capillary portion along an electrophoretic length of the supply capillary portion and the primary capillary portion while isolating the reaction chamber from the electrophoretic medium.

11. The combined reactor and analyzer of claim 9 in which the identification means includes:
- means for electrophoretically separating the reaction product by passage through an electrophoretic medium;
- a first laser for exciting the reacted sample in a portion of the electrophoretic medium with laser light that is selectively absorbed by the reaction product;
- a second laser for directing a beam of light at the reacted sample; and
- means for detecting deflection of the beam of light due to heating of the electrophoretic medium following excitation of the reaction product.

12. The combined reactor and analyzer of claim 9 further including a valve across the primary capillary portion between the reaction chamber and the junction between the supply capillary portion and the primary capillary portion, whereby isolation of the reaction chamber from the identification end of the primary capillary portion may be ensured.

13. The combined reactor and analyzer of claim 9 in which the reaction product holding means is formed from a cooling device disposed about the supply capillary portion.

14. The combined reactor and analyzer of claim 2 in which:
- the reaction product holding means is located at the primary capillary portion between the junction and the second fluid flow control means.

15. The combined reactor and analyzer of claim 14 in which:
- the second end of the supply capillary portion is connected to the primary capillary portion at the reaction end; and
- the third fluid flow control means includes a valve for directing fluids from the first fluid flow control means to one of the primary capillary portion and the supply capillary portion.

16. The combined reactor and analyzer of claim 14 in which the identification means includes:
- a laser for irradiating the reaction product in the primary capillary portion;
- means for detecting fluorescence from irradiation reaction product; and
- means for establishing an electric field in electrophoretic medium in the supply capillary portion and primary capillary portion along an electrophoretic length of the supply capillary portion and the primary capillary portion while isolating the reaction chamber from the electrophoretic medium.

17. The combined reactor and analyzer of claim 14 in which the identification means includes:
- means for electrophoretically separating the reaction product by passage through an electrophoretic medium;
- a first laser for exciting the reacted sample in a portion of the electrophoretic medium with laser light that is selectively absorbed by the reaction product;
- a second laser for directing a beam of light at the reacted sample; and
- means for detecting deflection of the beam of light due to heating of the electrophoretic medium following excitation of the reaction product.

18. The combined reactor and analyzer of claim 14 further including a valve across the primary capillary portion between the reaction chamber and the junction between the supply capillary portion and the primary capillary portion, whereby isolation of the reaction chamber from the identification end of the primary capillary portion may be ensured.

19. The combined reactor and analyzer of claim 14 in which the reaction product holding means is formed from a cooling device disposed about the supply capillary portion.

* * * * *